US 9,527,827 B2

(12) United States Patent
Joshi et al.

(10) Patent No.: US 9,527,827 B2
(45) Date of Patent: Dec. 27, 2016

(54) C-9 OXYGEN FUNCTIONALIZED LABDANE DERIVATES

(75) Inventors: Swati Joshi, Pune (IN); Roshan Rajan Kulkarni, Pune (IN); Ketaki Dilip Shurpali, Pune (IN); Sampa Sarkar, Pune (IN); Dhiman Sarkar, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/237,235

(22) PCT Filed: Aug. 6, 2012

(86) PCT No.: PCT/IN2012/000543
§ 371 (c)(1),
(2), (4) Date: Feb. 5, 2014

(87) PCT Pub. No.: WO2013/024493
PCT Pub. Date: Feb. 21, 2013

(65) Prior Publication Data
US 2014/0171498 A1      Jun. 19, 2014

(30) Foreign Application Priority Data
Aug. 5, 2011   (IN) .......................... 2224/DEL/2011

(51) Int. Cl.
*C07D 493/00*      (2006.01)
*C07D 307/94*      (2006.01)
*C07C 35/36*       (2006.01)
*C07D 493/10*      (2006.01)
*C07D 307/58*      (2006.01)

(52) U.S. Cl.
CPC ............. *C07D 307/94* (2013.01); *C07C 35/36* (2013.01); *C07D 307/58* (2013.01); *C07D 493/10* (2013.01); *C07C 2102/28* (2013.01)

(58) Field of Classification Search
CPC ... C07D 493/04; C07D 307/20; C07D 301/12; C07D 303/04
USPC ................................................. 549/464, 531
See application file for complete search history.

(56) References Cited

PUBLICATIONS

Database Registry [Online] Chemical Abstcts Service, Columbus, Ohio, US; "2-[2-[(2S,8aS)-dechydro-1-hydroxy-2,5,5,8a-tetramethyl-1-naphthalenyl]ethyl]-2-Butene-1,4-diol," (Jun. 29, 2010).

Database Registry [Online] Chemical Abstracts Service, Columbus, Ohio, US; "(27)-2-[2-[(1R,2R,8aR)-decahydro-1-hydroxy-2,5,5,8a-tetramethyl-1-naphthalenyl]ethyl]-2-Butene-1,4-diol," Apr. 16, 2009.

Elizabeth Nieto-Mendoza et al., "Electro-Oxidation of Hispanolone and Anti-Inflammatory Properties of the Obtained Derivatives," The Journal of Organic Chemistry, vol. 70, No. 11, pp. 4538-4541 (May 1, 2005).

Katara Antarikish et al., "PHytochemical Investigation an Antimicrobial Activity of Leucas Cephalotes Roth. Spreng Whole Herb," Der Pharmacia Lettre, vol. 2, No. 4, pp. 284-296.

Masateru Ono et al., "A New Diterpenoid Glucoside and Two New Dlterpenoids fro mteh Fruit of Vitex agnus-castus," Chemical and Pharmaceutical Bulletin (2011), vol. 59, No. 3, pp. 392-396 (Dec. 22, 2010).

Mangathayamru K et al., "Antimicrobial activity of *Leucas aspera* flowers," Fitoterapia, vol. 76, No. 7-8, pp. 752-754 (Dec. 1, 2005).

International Search Report from PCT/IN2012/000543 Nov. 14, 2012 (3 pages).

*Primary Examiner* — Noble Jarrell
(74) *Attorney, Agent, or Firm* — Abelman, Frayne & Schwab (57) ABSTRACT

This invention relates to diterpenes of general formula (1) belonging to labdane class, isolated from *Leucas stelligera*, being useful for prevention, treatment, inhibition or controlling growth and proliferation of mycobacterial activity in mammals. The invention further discloses process for isolation of the fractions containing the same.

12 Claims, 4 Drawing Sheets

C-9 OXYGEN FUNCTIONALIZED LABDANE DERIVATES

RELATED APPLICATIONS

This application is a §371 of PCT/IN2012/000543 filed Aug. 6, 2012, and claims priority from Indian Patent Application No. 2224/DEL/2011 filed Aug. 5, 2011, both incorporated by reference in their entirety.

TECHNICAL FIELD OF INVENTION

This invention relates to diterpenes of general formula 1 belonging to labdane class, isolated from *Leucas stelligera*, being useful for prevention, treatment, inhibition or controlling growth and proliferation of mycobacterial activity in mammals. The invention further discloses process for isolation of the fractions containing the same.

BACKGROUND AND PRIOR ART

*Tuberculosis* (TB) is a major and still neglected cause of death and disability with around 2 million deaths worldwide in 2009 and 9 million infections. There is more *tuberculosis* today than at any other time in history. The emergence of drug resistant strains and confluence with HIV epidemic has turned TB into a global public health crisis. Although, available drug regimens can cure most patients, emergence of MDR, SDR and XDR-TB coupled with insufficient global drug pipeline, justifies continued efforts towards development of new drugs with new mode of action and novel structures. It has therefore now become imperative to identify new lead molecules for the development of new tuberculostatic drugs.

Family Lamiaceae and diterpenes class of compounds, particularly from *Leucas* genus has been the subject matter of interest for the study of anti-tubercular drugs. Reference may be made to International Journal of Pharm Tech Research, ISSN: 0974-4304 Vol. 3, No. 2, pp 872-880, published in. April-June 2011 titled "A Review on Anti-Tubercular Plants" by Vikrant Arya et.al discloses various plant drugs along with their chemical constituents like alkaloids, flavonoids, tannins, xanthones, triterpenes, quinones etc. responsible for anti-tubercular activity. Table 2 in the said article gives a brief description of common anti-tubercular plants from Ayurveda. Table 3 lists anti-tubercular plants of foreign origin wherein, diterpenes are isolated from plant (i) *Salvia hypargeia* of family Lamiaceae and (ii) *Salvia sclarea* of Family Lamiaceae using alcohol as a solvent.

Article titled 'Antimycobacterial natural products' by Brent R. Copp in Nat. Prod. Rep., 2003, 20, 535-557, having DOI: 10.1039/b212154a discloses natural products having anti-TB activity. The article further discloses Terpenes with anti-TB activity. (i) Halogenated monoterpenes originally isolated from the marine red alga *Plocamium cartilagineum*, exhibits potent anti-algal activity as well as antimycobacterial activity towards *M. tuberculosis* H37Rv with an MIC of 32 µg/ml and *M. avium* (MIC 64 µg/ml). (ii) Also identified as exhibiting antitubercular (*M. tuberculosis* H37Rv) activity in this study were juniperexcelsic acid (MIC 14.4 µg/ml) (205) and sclareol (MIC6.0 µg/ml) (206).

205

206

Article titled "Phytochemical Investigation and Antimicrobial Activity of *Leucas cephalotes* (Roth.) Spreng. Whole Herb by Katara Antariksh et.al in Der Pharmacia Lettre, 2010, 2(4):284-296; discloses *Leucas cephalotes* Roth. Spreng (Lamiaceae) to cure various disorders. The plant has antipyretic action and also considered to be stimulant, expectorant, aperient, diaphoretic, insecticidal and emmenagogue. *Leucas cephalotes* (Roth.) Spreng. whole herb contains new labdane, norlabdane and abietane type diterpenes and protostane type triterpenes, together with common triterpene, five sterols and eight flavones.

Different extracts of the transverse section of stem, leaf and root were subjected to various phytochemical tests, to identify the active constituents, shown in Table 2 in the said article. Ethanolic and methanolic extracts were found to have more active constituents compared to other extracts. Phytochemicals such as carbohydrate, proteins and amino acids, glycosides, flavonoids, tannins and phenols and steroids were commonly found in most of the extracts. (However, the extracts do not mention diterpenes as a phytoconstituent).

Article titled "Diterpenes from *Leucas aspera* Inhibiting Prostaglandin-Induced Contractions" by Samir Kumar Sadhu et.al in J. Nat. Prod., 2006, 69 (7), pp 988-994 and having DOI: 10.1021/np058118m relates to four new diterpenes, leucasperones A (1) and B (2) and leucasperols A (3) and B (4), and three new isopimarane glycosides, leucasperosides A, B, and C (5-7), together with the known compounds asperphenamate, maslinic acid, (−)-isololiolide, and linifolioside. leucasperone A (1), leucasperosides A (5) and B (6), and linifolioside showed inhibition of prostaglandin-induced contractions.

Leucasperone A

In the search for such new molecules, a wide range of plant extracts were screened for their inhibitory potential against the *tuberculosis*. The extracts of *Leucas stelligera* unexpectedly showed most potent anti-tubercular property among the extracts tested. *Leucas stelligera* is an edible plant with leaves eaten as vegetable. No chemical and pharmacological work is reported on this species.

OBJECTIVE OF THE INVENTION

Main objective of the present invention is to provide compounds of general formula 1 isolated from *Leucas stelligera* useful for the treatment of *Mycobacterium tuberculosis*.

Another object of the present invention is to provide a process for isolation and characterization of diterpene compounds from *Leucas stelligera*.

SUMMARY OF THE INVENTION

Accordingly, the present invention provides diterpenes of general formula 1 belonging to labdane class, isolated from *Leucas stelligera*

Formula 1

In an embodiment of the present invention compounds of general formula 1 wherein said compound is represented by group of the following compounds Compound 1:

9(S)-Hydroxylabd-13(14)-en-15,16-olide.

Compound 2:

Labd-9,13,15,16-diepoxy-15α-ol

Compound 3:

Labd-13(14)-en-9α,15,16-triol

In another embodiment of the present invention Compounds of general formula 1 are useful for prevention, treatment, inhibition or controlling growth and proliferation of tubercular activity in mammals.

In yet another embodiment of the present invention Compounds of general formula 1 as claimed in claim 1, wherein IC50 value is in the range of 5.02 to 9.8 µg/ml against *Mycobacterium tuberculosis*.

In still another embodiment of the present invention Compounds of general formula 1 as claimed in claim 1, wherein IC90 value is in the range of 10.7 to 46.52 µg/ml against *Mycobacterium tuberculosis*.

Another embodiment of the present invention a process for the extraction of compounds of general formula 1, wherein the said process comprising the step of:
  i. Powdering aerial parts of *L. stelligera* followed by extraction with acetone at a temperature in the range of 25 to 30° C., filtering acetone solubles and concentrating under reduced pressure in the range of 50-100 mm Hg to obtain a greenish acetone extract, ii. separating the extract of step i) by using column chromatography (CC) with gradient increasing polarity of the 10-50% acetone in pet ether to obtain 11 fractions (LS-1 to LS-11),
iii. subjecting fraction LS7 of step ii) to CC with gradient of acetonitrile from 1% to 3% in chloroform to obtain 18 sub-fractions (LS7a-r),
iv. subjecting sub-fraction LS7i of step iii) to CC in 15% acetone in petroleum ether to obtain compound 1 and 4,
v. subjecting fraction LS4 of step ii) to CC in 6% acetonitrile in chloroform to obtain 10 (LS4a-j) sub-fractions,
vi. subjecting fraction LS5 of step ii) to CC in 6% acetonitrile in chloroform to obtain 13(L S5a-m) sub-fractions,
vii. combining fractions LS4f, LS4h, LS4i of step v) and LS5j, LS5k of step vi) and subjecting to CC in 15% acetone-petroleum ether to obtain compound 2,
viii. subjecting fraction LS11 of step ii) to CC in gradient of methanol from 5-20% in chloroform to obtain 8 fractions (LS11a-h),
ix. subjecting sub-fraction LS11b of step viii) to CC in gradient of methanol in chloroform from 1-3% to obtain 6 (LS11bi-bvi) sub-fractions,
x. subjecting sub-fraction LS11bvi of step ix) to CC in gradient of acetone from 5-50% in petroleum ether to obtain further sub-fractions including sub-fraction LS11bvia,
xi. subjecting sub-fraction LS11bvia of step x) to successive preparative thin layer chromatographies (PTLC) in 25% acetonitrile in chloroform and 35% ethyl acetate in chloroform to obtain compound 3.

In still another embodiment of the present invention a pharmaceutical composition comprising a compound selected from the group of general formula 1 and a pharmaceutically acceptable carrier.

DESCRIPTION OF FIGURES

FIG. 1:
FIG. 2:
FIG. 3:
FIG. 4.

DETAILED DESCRIPTION OF INVENTION

Figure 1A:
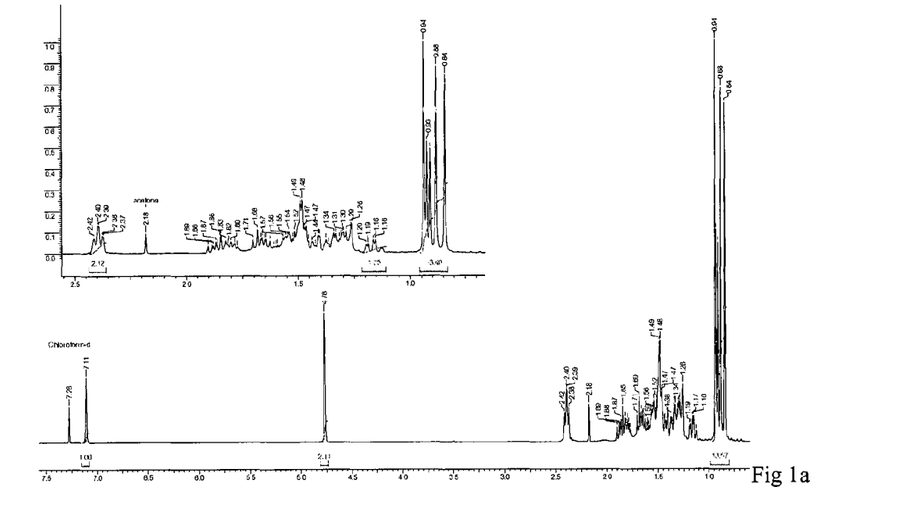
FIG. 1a gives $^1$HNMR of compound 1
FIG. 1b gives $^{13}$CNMR of compound 1 with DEPT in inset.
Figure 1B:
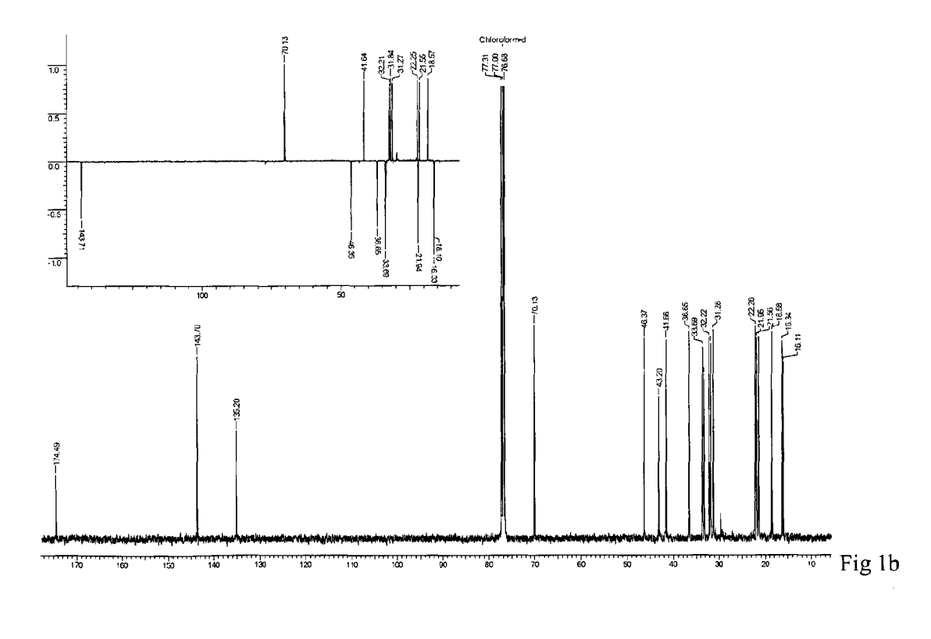
Figure 2A:
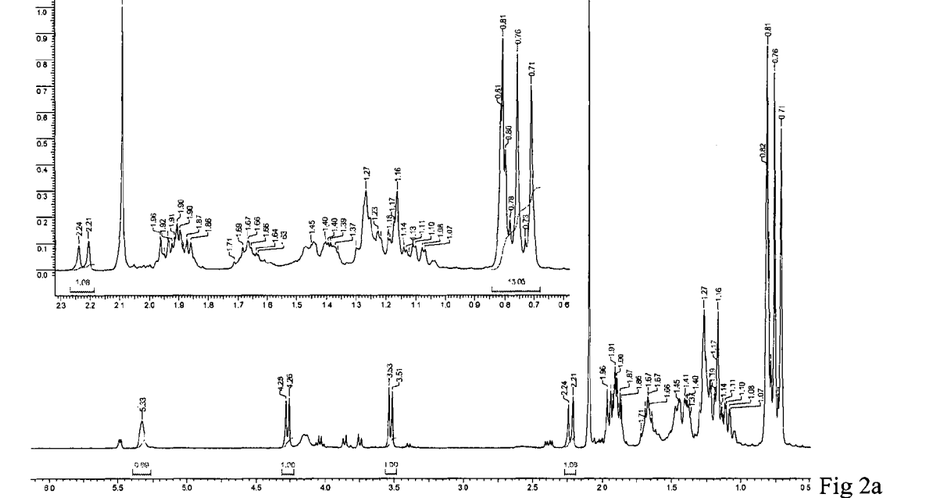
FIG. 2a gives $^1$HNMR of compound 2
FIG. 2b gives $^{13}$CNMR of compound 2 with DEPT in inset.
Figure 2B:
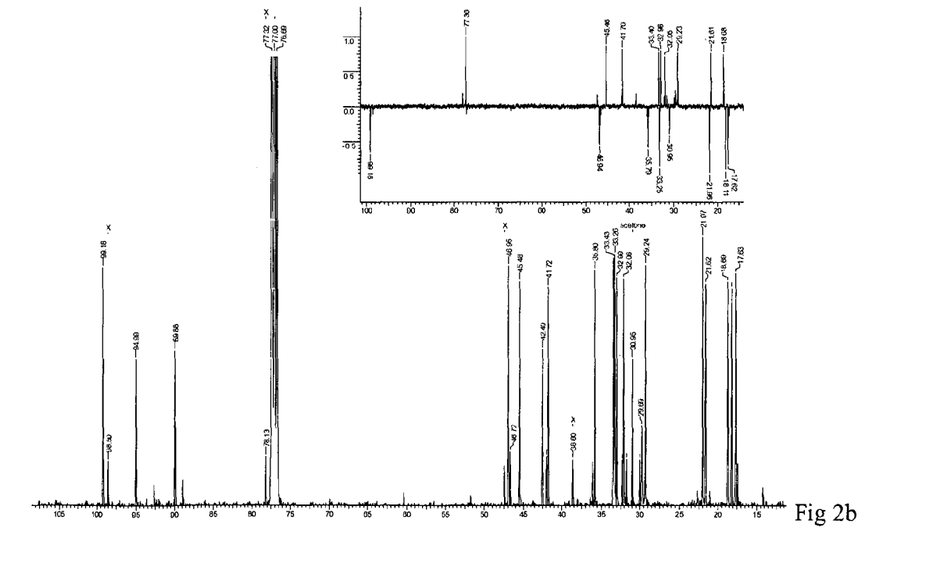
Figure 3A:
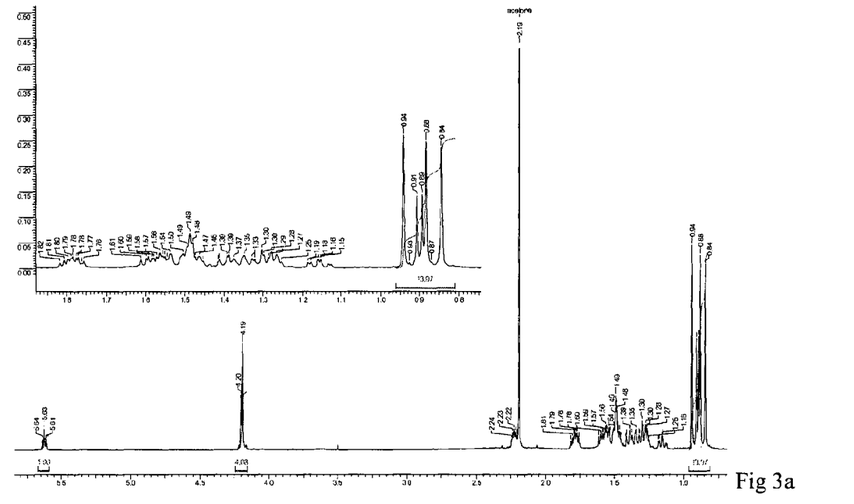
FIG. 3a gives $^1$HNMR of compound 3
FIG. 3b gives $^{13}$CNMR of compound 3 with DEPT in inset.
Figure 3B:
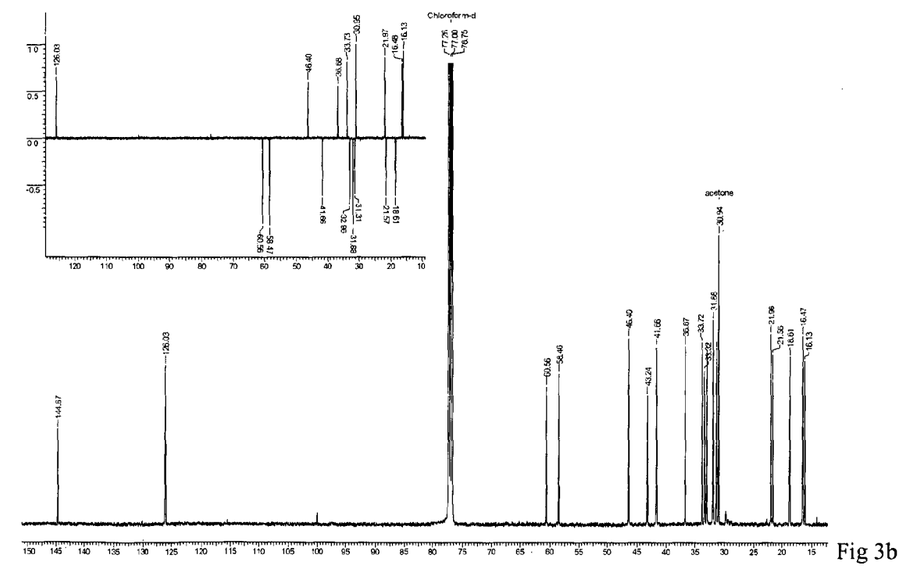
Figure 4A:
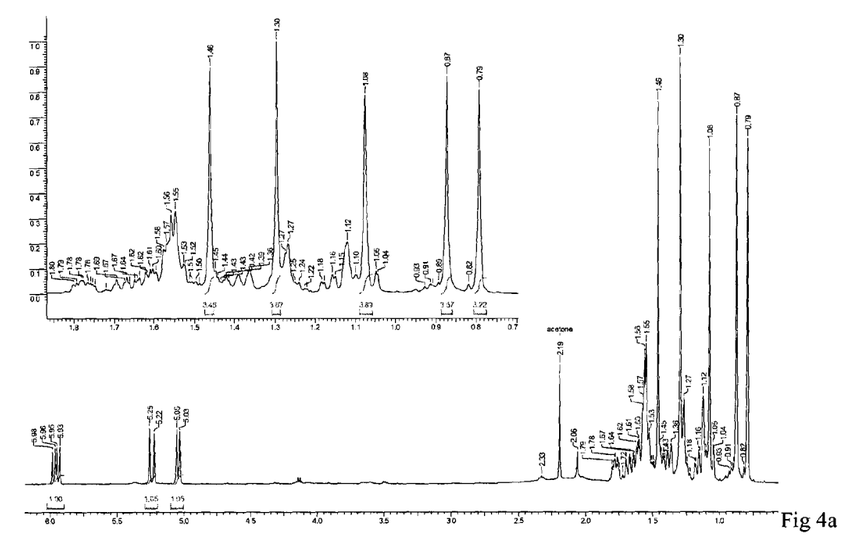
FIG. 4a gives $^1$HNMR of compound 4
FIG. 4b gives $^{13}$CNMR of compound 4 with DEPT in inset.
Figure 4B:
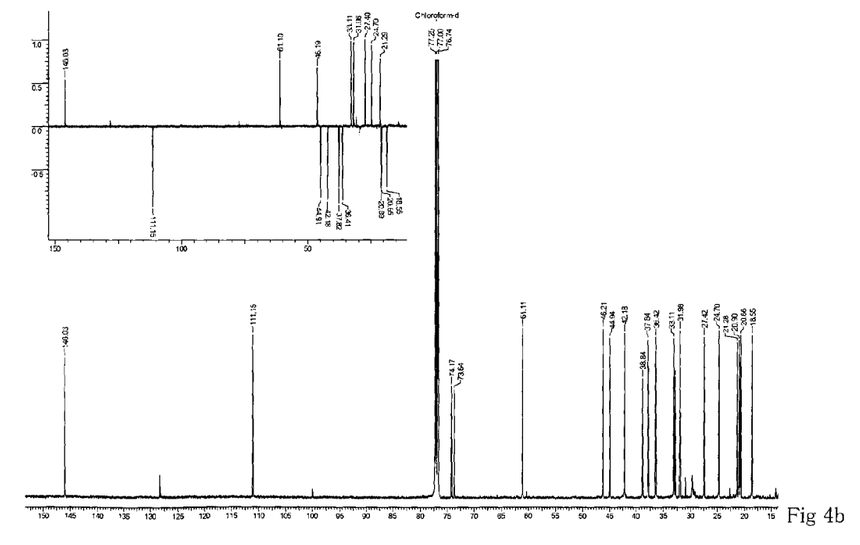

Entire mature plants of *Leucas stelligera*, in flowering, are collected from agricultural fields from Mulshi area, District, Pune on 3 Jan. 2008. A herbarium is deposited in Botanical Survey of India, Western Circle, Pune (voucher no. SPJ-5). Plant material is cleaned off adhering dust and unwanted plant material, roots are removed, aerial parts dried in shade, cut and pulverized. Powdered plant material is extracted with aetone to prepare acetone extract. From the acetone extract, active compounds 1- 4 are isolated as shown in scheme 1.

Scheme 1

In one preferred embodiment, the pulverized aerial parts of *Leucas stelligera* are subject to acetone extraction; separation of fractions and isolation of diterpenes belonging to Labdane class from sub fractions are depicted in Scheme 1 as above. The acetone extract of the aerial parts of *L. stelligera* by repeated chromatography resulted in the isolated 4 compounds all of which are diterpenes belonging to Labdane class. The structures of the compounds as confirmed by NMR (Tables 1 and 2) are enlisted here in Formula 1.

Compound 1: $R_1$             $R_2 = OH$

Compound 2: $R_1$ and $R_2$

Compound 3: $R_1$             $R_2 = OH$

Compound 4

The compounds are isolated from the fractions/extracts using at least one separation technique selected from partition(s), precipitation(s), crystallization, normal phase chromatography, reversed phase chromatography, size exclusion chromatography and ion exchange chromatography or combinations thereof.

All the compounds 1 to 4 isolated are characterized by NMR, the details of which is provided in Tables 1 and 2.

TABLE 1

$^{13}C$ NMR shifts for compounds 1, 2, 3 and 4.

| Position | 1 | 2 | 3 | 4 |
|---|---|---|---|---|
| 1 | 31.8, $CH_2$ | 33.0, $CH_2$ | 31.9, $CH_2$ | 36.5, $CH_2$ |
| 2 | 18.6, $CH_2$ | 18.7, $CH_2$ | 18.6, $CH_2$ | 18.6, $CH_2$ |
| 3 | 41.6, $CH_2$ | 41.8, $CH_2$ | 41.7, $CH_2$ | 42.2, $CH_2$ |
| 4 | 33.3, C | 33.5, C | 33.3, C | 32.9, C |
| 5 | 46.3, CH | 47.0, CH | 46.4, CH | 46.2, CH |
| 6 | 21.5, $CH_2$ | 21.7, $CH_2$ | 21.6, $CH_2$ | 20.7, $CH_2$ |
| 7 | 31.2, $CH_2$ | 32.1, $CH_2$ | 31.3, $CH_2$ | 37.8, $CH_2$ |
| 8 | 36.6, CH | 35.8, CH | 36.9, CH | 74.2, C |
| 9 | 76.8, C | 95.0, C | 77.3, C | 61.2, CH |
| 10 | 43.2, C | 42.5, C | 43.2, C | 38.9, C |
| 11 | 32.2, $CH_2$ | 29.3, $CH_2$ | 33.0, $CH_2$ | 20.9, $CH_2$ |
| 12 | 22.2, $CH_2$ | 33.4, $CH_2$ | 31.9, $CH_2$ | 45.0, $CH_2$ |
| 13 | 135.1, CH | 89.9, C | 144.7, C | 73.6, C |
| 14 | 143.7, C | 45.5, $CH_2$ | 126.0, C | 146.2, CH |
| 15 | 70.1, $CH_2$ | 99.2, CH | 60.6, $CH_2$ | 111.1, $CH_2$ |
| 16 | 174.5, C | 77.3, $CH_2$ | 58.5, $CH_2$ | 27.3, $CH_3$ |
| 17 | 16.2, $CH_3$ | 17.7, $CH_3$ | 16.5, $CH_3$ | 32.0, $CH_3$ |
| 18 | 33.7, $CH_3$ | 22.0, $CH_3$ | 33.7, $CH_3$ | 33.1, $CH_3$ |
| 19 | 22.0, $CH_3$ | 33.3, $CH_3$ | 22.0, $CH_3$ | 21.4, $CH_3$ |
| 20 | 16.3, $CH_3$ | 18.2, $CH_3$ | 16.2, $CH_3$ | 24.8, $CH_3$ |

TABLE 2

$^1H$ NMR shifts for compounds 1, 2, 3 and 4.

| Position | 1 | 2 | 3 | 4 |
|---|---|---|---|---|
| 1 | 1.49 (m) | 1.36 m | 1.48 m | 1.10 m, 1.57 m |
| 2 ax | 1.48 m | 1.55 m | 1.55 m, 1.48 m | 1.68 m |
| 2 eq | 1.48 m | 1.48 m | | 1.43m |
| 3 ax | 1.16 dt (3.5, 12.9) | 1.17 dt (3.6, 13.0) | 1.15 dt (3.5, 13.2) | 1.15 dt (3.92, 13.62) |
| 3 eq | 1.34 m | 1.33 m | 1.35 m | 1.37 m |
| 4 | — | — | — | — |
| 5 | 1.42 m | 1.37 m | 1.39 m | 1.06 dd (12.64, 2.76) |
| 6 ax | 1.54 m | 1.55 m | 1.53 m | 1.55 m |
| 6 eq | 1.29 m | 1.27 m | 1.28 m | 1.25 m |
| 7 α | 1.49 m | 1.48 m | 1.27 m | 1.55 m |
| 7 β | 1.29 m | 1.22 m | 1.27 m | 1.55 m |
| 8 | 1.79 m | 1.76 m | 1.78 m | — |
| 9 | — | — | — | 1.11 |
| 10 | — | — | — | — |
| 11 | 1.66 m, 1.85 m | 1.76 m, 2.03 m | 1.78 m, 1.57 m | 1.78 m, 1.50 m |
| 12 | 2.39 dt (1.34, 8.43) | 2.00 (m) | 2.2 m | 1.52-1.63 m |
| 13 | — | — | — | — |
| 14 | 7.11 bt (1.6) | 2.32 d (13.10), 1.98 m | 5.63 t (6.91) | 5.95 dd (17.30, 10.38) |
| 15 | 4.77 bq (1.99) | 5.43 bs | 4.19 bs | 5.22 (d, 17.30), 5.03 d (10.38) |
| 16 | — | 4.37 d (8.5), β3.62 d (8.5) | 4.20 bs | 1.29 s |
| 17 | 0.92 d (6.65) | 0.91 d (6.62) | 0.89 d (6.99) | 1.47 s |
| 18 | 0.88 s | 0.81 s | 0.88 s | 0.87 s |
| 19 | 0.84 s | 0.86 s | 0.84 s | 0.79 s |
| 20 | 0.94 s | 0.91 s | 0.94 s | 1.07 s |

In a preferred embodiment the novel labdane class of the invention were evaluated for their anti-tubercular activity. Three compounds, 1, 2 and 3 are found to be specifically active against *Mycobacterium*. The compounds are also evaluated for cytotoxicity as exemplified herein and found to be non toxic. Compound 4 is also found to have potent anti-tubercular activity.

The following examples, will serve to illustrate the practice of this invention, it being understood that the particulars shown are by way of example and for purpose of illustrative discussion of preferred embodiments of the invention.

EXAMPLE 1

Powdered aerial parts of *L. stelligera* (1.8 kg) were extracted with acetone (3×3 L, 14 h) at a temperature of 25 to 30° C. The mixture was filtered and concentrated under reduced pressure to provide a greenish acetone extract of 57.0 g, 55.0 g of which was further purified by column chromatography (CC) with increasing polarity of acetone from 10 to 50%, in petroleum ether to give 11 fractions (LS1-LS11).

Fraction LS7 (4.1 g) was further subjected to CC with acetonitrile from 1% to 3% in chloroform to give 18 sub-fractions (LS7a-r). Sub-fraction LS7i (287.2 mg) was further subjected to CC in 15% acetone in petroleum ether to give compound 1 (120 mg) and 4 (35 mg).

Fraction LS4 (5.5 g) and LS5 (2.3 g) were further subjected to CC in 6% acetonitrile in chloroform to give 10 (LS4a-j) and 13 (LS5a-m) sub-fractions respectively. Fractions LS4f, LS4h, LS4i and LS5j, LS5k were pooled and further subjected to CC in 15% acetone-petroleum ether to give compound 2 (150 mg).

Fraction LS11 (4.9 g) was further subjected to CC in gradient of methanol from 5-20% in chloroform to give 8 fractions (LS11a-h). Sub-fraction LS11b (3 g) was further subjected to CC in methanol-chloroform from 1-3% to give 6 (LS11bi-bvi) sub-fractions.

Sub sub-fraction LS11bvi (300 mg) was further subjected to CC in gradient of acetone from 5-50% in petroleum ether to obtain further sub fractions including LS11bvia. Sub fraction LS11bvia was purified by successive preparative thin layer chromatography (PTLC) in 25% acetonitrile in chloroform and 35% ethyl acetate in chloroform to give compound 3 (20 mg).

EXAMPLE 2

Anti-Mycobacterial Activities of Compounds 1, 2, 3 and 4

All the isolated compounds and whole acetone extract were tested for their in vitro effect against *Mycobacterium tuberculosis* H37Ra. Compounds 1, 2, 3 and 4 showed significant inhibition against *Mycobacterium tuberculosis* H37Ra. The $IC_{50}$ and $IC_{90}$ values for the same are shown in Table 3.

To check the specificity of these compounds, Compounds 1, 2 and 3 were also tested at these $IC_{90}$ values against *Escherichia coli* and *Mycobacterium smegmatis*, using cultures maintained in-house. The percent inhibition values are given in Table 4.

Protocol for Activity Against *M. smegmatis*:

On the 3rd day of incubation, the microplate was taken out to remove the seal and measure the viable cells. Optical density was measured before addition of XTT at 470 nm. 200 μM XTT was added and incubated for 20 min at 37° C. after shaking for 1 min. After 20 min incubation, 60 μM menadione was added and mixed for 1 min and then incubated at 37° C. for another 20 min. The optical density was measured at 470 nm by using a micro plate reader. For Hypoxia induced XTT reduction microplate assay (HXRMA) on the 7th day of incubation, the plates were taken out and the seal was removed. A similar protocol as mentioned above was repeated for aerobically grown *M. smegmatis*.

Protocol for Activity Against *E. coli*:

The effect on growth was calculated by measuring the absorbance of culture at 620 nm after an incubation time of 6 h.

Results:

These compounds did not show any significant effect on *E. coli* and *M. smegmatis*, thus indicating the specificity of these compounds against pathogenic mycobacteria.

TABLE 3

In vitro anti-mycobacterial activity of 1-4 and acetone extract against *M. tuberculosis*

| Samples | $IC_{50}$ (μg/ml) | $IC_{90}$ (μg/ml) |
|---|---|---|
| 1 | 5.02 | 19.67 |
| 2 | 5.55 | 14.88 |
| 3 | 9.8 | 46.52 |
| 4 | 5.95 | 10.85 |
| Extract | 8.94 | 43.98 |
| Isoniazid |  | 0.05 ± 0.003 |

TABLE 4

Percent inhibition values of 1-4 and acetone extract showing biological activities

| Samples* | *M. smegmatis* | *E. coli* |
|---|---|---|
| 1 | 31.56 ± 6.09 | 0.29 ± 3.56 |
| 2 | 47.83 ± 3.74 | 23.15 ± 2.45 |
| 3 | 30.57 ± 3.58 | 11.47 ± 1.65 |
| Extract | 19.47 ± 0.16 | 3.48 ± 2.561 |
| Rifampicin** | 0.2 ± 0.03 | 0.5 ± 0.04 |

*Compounds tested at $IC_{90}$ found against *M. tuberculosis*
**$IC_{90}$, μg/ml The experiment was carried out three times and the results are mean±S. D.

EXAMPLE 3

Composition (i)
Compound of formula 1 (viz., Compound for Compound 2 or Compound 3): 10.0% w/w
FDA approved colour: 0.3% w/w
FDA approved flavor: 0.7% w/w
Magnesium stearate: 2.0% w/w Mannitol: q.s. to 100.0%w/w Procedure: Dissolve mannitol in water, add color and flavor to it. Evaporate water to adsorb color and flavor on mannitol. Mix active ingredient and Magnesium stearate and fill in pouch or bottle.

Mode of Administration

Disperse the powder in water/juice.

Composition (ii)

| Corosolic acid | 5.0% w/w |
| FDA approved colour | 0.3% w/w |
| FDA approved flavor | 0.7% w/w |
| Magnesium stearate | 2.0% w/w |
| Mannitol | q.s. to 100.0% w/w |

Procedure: Dissolve mannitol in water, add color and flavor to it. Evaporate water to adsorb color and flavor on mannitol. Mix active ingredient and Magnesium stearate and may be filled in a capsule of suitable size.

Mode of Administration:

The capsule may be had with water or juice.

Advantages of Present Invention

After assaying the compounds 1, 2, 3, and 4 of the present invention, these compounds are found to be effective against *Mycobacterium tuberculosis* due to their anti-tubercular property.

Compounds 1, 2 and 3 were fond to be selective inhibitors of *M. tuberculosis*.

The plant of the present investigation is edible and with the source anti-TB activity identified, it holds a promising for being used in the treatment of *tuberculosis*.

Compound 4 belongs to the novel class of compounds called cis-labdane.

We claim:

1. A composition comprising a compound of formula:

wherein $R_1$ and $R_2$ are together:

and a pharmaceutically acceptable carrier, enclosed in a capsule.

2. A composition comprising a compound of formula:

wherein $R_1$ is:

and $R_2$ is OH and a pharmaceutically acceptable carrier, enclosed in a capsule.

3. A method for inhibition, control of growth or proliferation of tubercular bacteria selected from the group consisting of *M. tuberculosis* and *M. smegmatis* comprising contacting said tubercular bacteria with an amount of the composition of claim 1, or 2 sufficient to inhibit, control growth, or control proliferation of said tubercular bacteria.

4. The method of claim 3, carried out in vitro.

5. A process for the extraction of a compound of formula:

wherein $R_1$ is:

and $R_2$ is OH comprising i) powdering aerial parts of *Leucas steiligera* followed by extraction with acetone at room temperature in the range of 25 to 30° C., filtering acetone solubles and concentrating under reduced pressure in the range of 50-100 mm Hg to obtain a greenish acetone extract, ii) separating the extract of step i) by using column chromatography (CC) with gradient increasing polarity of 10-50% acetone in petroleum ether to obtain 11 fractions (LS1 to LS-11), iii) subjecting fraction LS7 of step ii) to CC with a gradient of acetonitrile from 1% to 3% in chloroform to give 18 sub-fractions (LS7a-4), iv) subjecting sub-fraction LS7i of step iii) to CC in 15% acetone in petroleum ether to obtain said compound.

6. A process for the extraction of a compound of formula:

wherein $R_1$ and $R_2$ are together:

comprising:

i) powdering aerial parts of *Leucas stelligera* followed by extraction with acetone at room temperature in the range of 25 to 30° C., filtering acetone solubles and concentrating under reduced pressure in the range of 50-100 mm Hg to obtain a greenish acetone extract, ii) separating the extract of step i) by using column chromatography (CC) with gradient increasing polarity of the 10-50% acetone in petroleum ether to obtain 11 fractions (LS-1 to LS-11), iii) subjecting fraction LS7 of step ii) to CC with gradient of acetonitrile from 1% to 3% in chloroform to give 18 sub-fractions (LS7a-r), iv) subjecting sub-fraction LS7i of step iii) to CC in 15% acetone in petroleum ether, v) subjecting fraction LS4 of step ii) to CC in 6% acetonitrile in chloroform to give 10 (LS4a-j) sub-fractions, vi) subjecting fraction LS5 of step ii) to CC in 6% acetonitrile in chloroform to give 13(LS5a-m) sub-fractions, and vii) combining fractions LS4f, LS4h, LS4i of step v) and LS5j, LS5k of step vi) and subjecting to CC in 15% acetone-petroleum ether to obtain the compound of claim 1.

7. A process for the extraction of a compound of formula wherein $R_1$ is;

and $R_2$ is OH
comprising:

i) powdering aerial parts of *Leucas stelligera* followed by extraction with acetone at room temperature in the range of 25 to 30° C., filtering acetone solubles and concentrating under reduced pressure in the range of 50-100 mm Hg to obtain a greenish acetone extract, ii) separating the extract of step i) by using column chromatography (CC) with gradient increasing polarity of the 10-50% acetone in petroleum ether to obtain 11 fractions (LS-1 to LS-11), iii) subjecting fraction LS7 of step ii) to CC with gradient of acetonitrile from 1% to 3% in chloroform to give 18 sub-fractions (LS7a-r), iv) subjecting sub-fraction LS7i of step iii) to CC in 15% acetone in petroleum ether, v) subjecting fraction LS4 of step ii) to CC in 6% acetonitrile in chloroform to obtain 10 (LS4a-j) sub-fractions, vi) subjecting fraction LS5 of step ii) to CC in 6% acetonitrile in chloroform to obtain 13 (LS5a-m) sub-fractions, vii) combining fractions LS4f, LS4h, LS4i of step v) and LS5j, LS5k of step vi) and subjecting to CC in 15% acetone-petroleum ether, viii) subjecting fraction LS11 of step ii) to CC in gradient of methanol from 5-20% in chloroform to obtain 8 fractions (LS11a-h), ix) subjecting sub-fraction LS11b of step viii) to CC in gradient of methanol in chloroform from 1-3% to give 6 (LS11bi-bvi) sub-fractions, x) subjecting sub-fraction LS11bvi of step ix) to CC in gradient of acetone from 5-50% in petroleum ether, xi) subjecting fraction 1 of step x) to successive preparative thin layer chromatographies (PTLC) in 25% acetonitrile in chloroform and 35% ethyl acetate in chloroform to obtain the compound of claim 2.

8. The composition of claim 1, wherein said pharmaceutically acceptable carrier is mannitol.

9. The composition of claim 2, wherein said pharmaceutically acceptable carrier is mannitol.

10. The composition of claim 1, wherein said pharmaceutically acceptable carrier is magnesium stearate.

11. The composition of claim 2, wherein said pharmaceutically acceptable carrier is magnesium stearate.

12. A method for inhibition, control of growth or proliferation of tubercular bacteria selected from the group consisting of *M. tuberculosis* and *M. smeginatis* comprising contacting said tubercular bacteria with a compound selected from the group consisting of:

I wherein $R_1$ is and $R_2$ is OH,

II wherein $R_1$ and $R_2$ are together:

and

III wherein $R_1$ is:

and $R_2$ is OH sufficient to inhibit, control growth, or control proliferation of said tubercular bacteria.

* * * * *